US008857441B2

(12) United States Patent  
Matsuo et al.

(10) Patent No.: US 8,857,441 B2  
(45) Date of Patent: Oct. 14, 2014

(54) BIOLOGICAL TISSUE TRANSFER METHOD AND BIOLOGICAL TISSUE TREATMENT METHOD

(75) Inventors: Nobuko Matsuo, Tokyo (JP); Takahiro Kogasaka, Tokyo (JP); Kunihide Kaji, Tokyo (JP); Ken Yamatani, Tokyo (JP); Seigo Kitano, Beppu (JP); Kazuhiro Yasuda, Oita (JP)

(73) Assignee: Olympus Medical Systems Corp., Tokyo (JP)

( * ) Notice: Subject to any disclaimer, the term of this patent is extended or adjusted under 35 U.S.C. 154(b) by 492 days.

(21) Appl. No.: 13/178,976

(22) Filed: Jul. 8, 2011

(65) Prior Publication Data

US 2012/0006337 A1 Jan. 12, 2012

Related U.S. Application Data

(60) Provisional application No. 61/362,891, filed on Jul. 9, 2010.

(51) Int. Cl.
   *A61B 19/00* (2006.01)
   *A61B 17/04* (2006.01)
   *A61B 1/32* (2006.01)
   *A61B 17/02* (2006.01)
   *A61B 17/00* (2006.01)
   *A61B 17/062* (2006.01)

(52) U.S. Cl.
   CPC ... *A61B 17/0218* (2013.01); *A61B 2017/00278* (2013.01); *A61B 2017/00818* (2013.01); *A61B 17/0469* (2013.01); *A61B 17/062* (2013.01)
   USPC ............................. 128/898; 606/232; 600/201

(58) Field of Classification Search
   CPC ................. A61B 17/0218; A61B 17/0469

USPC ........ 606/232, 233; 623/23.65; 600/101, 201, 600/204, 206, 209, 213, 215, 217, 218, 219, 600/235; 128/898
   See application file for complete search history.

(56) References Cited

U.S. PATENT DOCUMENTS 7,892,214 B2 * 2/2011 Kagan et al. .................. 604/264
7,946,976 B2 * 5/2011 Gertner ........................... 600/37
(Continued)

FOREIGN PATENT DOCUMENTS

JP 2001-61843 3/2001

OTHER PUBLICATIONS

"Peritoneum". Quizlet. Peritoneum Flashcards. Downloaded from <http://quizlet.com/7236908/peritoneum-flash-cards/> on Jan. 2, 2014.*

*Primary Examiner* — Andrew Iwamaye
(74) *Attorney, Agent, or Firm* — Scully, Scott, Murphy & Presser, PC

(57) ABSTRACT

The present application relates to a biological tissue transfer method for transferring a biological target tissue within the body, the method comprising: (a) attaching part of a first traction member to a first position which is different from a connecting position at which the target tissue is connected to other biological tissue; (b) attaching part of a second traction member to a second position which serves as the apex of a triangle formed together with the connecting position and the first position that surrounds the target site; (c) extending the first traction member in the direction from the connecting position to the first position, and extending the second traction member in the direction from the connecting position to the second position; and (d) transferring the target tissue within the body by applying traction on the first traction member and the second traction member respectively.

11 Claims, 17 Drawing Sheets

(56) References Cited

U.S. PATENT DOCUMENTS

| | | | |
|---|---|---|---|
| 8,257,365 B2* | 9/2012 | Demarais et al. | 606/139 |
| 2004/0078054 A1* | 4/2004 | Biggs et al. | 606/232 |
| 2004/0122456 A1* | 6/2004 | Saadat et al. | 606/157 |
| 2005/0267533 A1* | 12/2005 | Gertner | 606/232 |
| 2006/0135971 A1* | 6/2006 | Swanstrom et al. | 606/153 |
| 2007/0167680 A1 | 7/2007 | Miyamoto et al. | |
| 2007/0208360 A1* | 9/2007 | Demarais et al. | 606/153 |
| 2007/0233170 A1* | 10/2007 | Gertner | 606/192 |
| 2009/0312597 A1* | 12/2009 | Bar et al. | 600/37 |
| 2010/0160937 A1* | 6/2010 | Starksen | 606/157 |

* cited by examiner

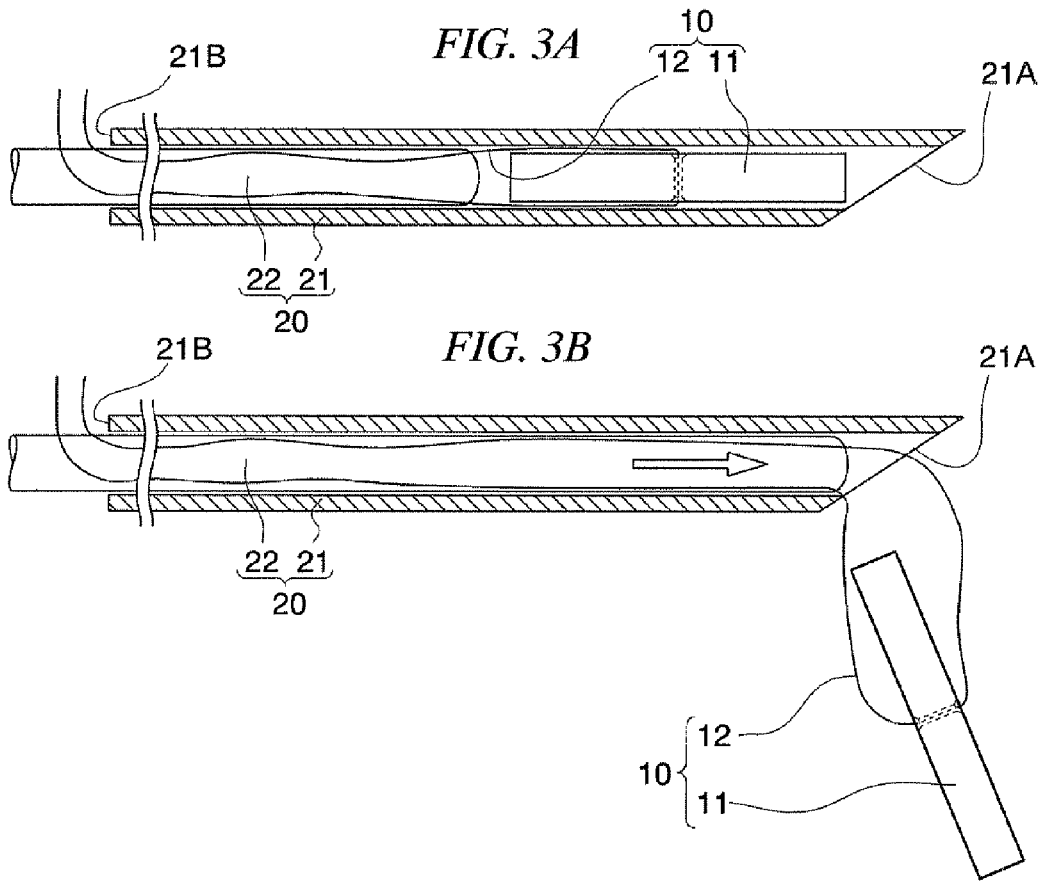
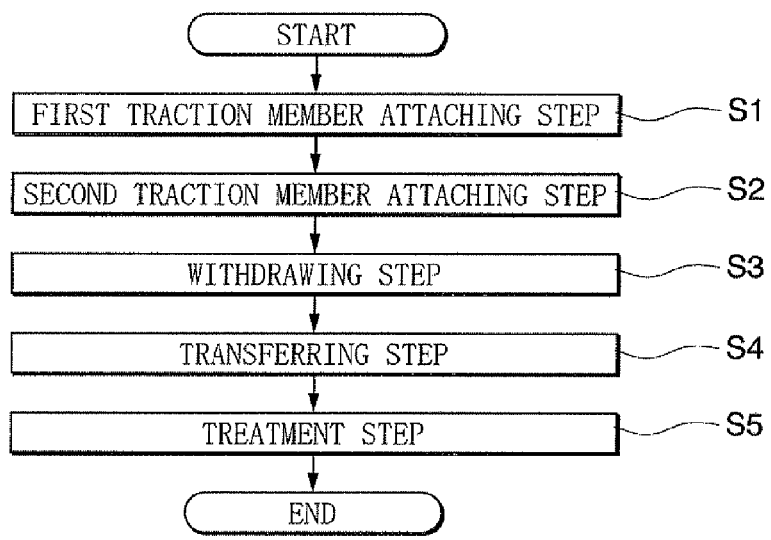

BIOLOGICAL TISSUE TRANSFER METHOD AND BIOLOGICAL TISSUE TREATMENT METHOD

Priority is claimed on U.S. Preliminary Patent Application No. 61/362,891, filed Jul. 9, 2010, the content of which is incorporated herein by reference.

BACKGROUND OF THE INVENTION

1. Field of the Invention

The present invention relates to a method for transferring biological tissue within the body, and to a treatment method for treating biological tissue.

2. Description of Related Art

Conventionally, a laparotomy has been performed when carrying out surgical treatment of a biological tissue inside the body. However, the use of laparoscopy to perform such treatments has become increasing common in recent years. In this technique, a small incision is made in the body wall to form a penetrating hole, and a laparoscope is then passed through this penetrating hole and into the body cavity.

Moreover, in recent years, methods have been carried out which do not require making a small incision in the body wall; rather, an endoscope is introduced into the patient's body through insertion via a natural orifice such as the mouth or anus, and a penetrating hole is made in the wall of a digestive organ, for example, for the purpose of introducing the endoscope into the body cavity. In this method, the biological tissue is then treated by introducing the endoscope and treatment instruments are introduced into the body cavity via the penetrating hole. The use of a medical treatment endoscope such as disclosed in U.S. Patent Application, Publication No. 2007/0167680, for example, has been proposed for this type of technique.

SUMMARY OF THE INVENTION

The present invention employs the constitutions described below.

One aspect of the present invention is related to a biological tissue transfer method for transferring within the body a biological target tissue on which a treatment target site is present, the method including:

(a) attaching part of a first traction member to a first position which is different from the target site on the target tissue, and which is different from a connecting position at which the target tissue is connected to other biological tissue which supports the target tissue within the body;

(b) attaching part of a second traction member to a second position which is different from the target site and the first position on the target tissue, and which serves as the apex of a triangle formed together with the connecting position and the first position that surrounds the target site;

(c) extending the first traction member in the direction from the connecting position to the first position, and extending the second traction member in the direction from the connecting position to the second position; and (d) transferring the target tissue within the body by applying traction on the first traction member and the second traction member respectively in the directions extending from the first traction member and the second traction member respectively.

BRIEF DESCRIPTION OF THE FIGURES

FIG. 3A is a cross-sectional view showing the structure of the indwelling instrument for fixing the traction member to the target tissue.

FIG. 3B is a view for explaining the action during use of the same indwelling implement.

FIG. 4 is a flow chart for explaining the steps in the same biological tissue transfer method and the biological tissue treatment method using this biological tissue transfer method.

DETAILED DESCRIPTION OF THE INVENTION

The biological tissue transfer method and the biological tissue treatment method according to one embodiment of the present invention will now be explained.

Figure 1:
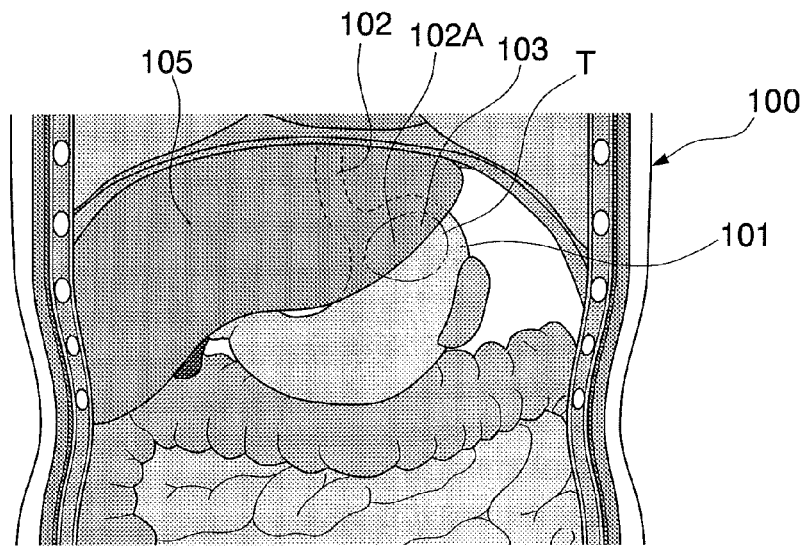
FIG. 1 is an anatomical diagram showing the abdomen of the patient to be treated, and is a schematic view for explaining the biological tissue transfer method and the biological tissue treatment method employing this same biological tissue transfer method according to a first embodiment of the present invention.

First, an overview of the biological tissue transfer method and the biological tissue treatment method according to the embodiment will be explained with reference to FIG. 1. FIG. 1 is a schematic view for explaining the biological tissue transfer method and the biological tissue treatment method using this biological tissue transfer method according to the first embodiment of the present invention. FIG. 1 is an anatomical diagram showing the abdomen of patient 100 on which the procedure is to be performed.

The biological tissue transfer method according to this embodiment is a method for securing space within the body in order to carry out a procedure on a biological tissue (referred to as "target tissue 101" hereinafter), by transferring target tissue 101 inside the body. Specifically, an endoscope, etc. is inserted via a natural orifice of the patient 100, a penetrating hole is formed in the wall of a digestive organ, and the endoscope, etc., is introduced into the body cavity by passage through this penetrating hole. The biological tissue transfer method according to the present embodiment can be optimally employed in a technique for treating a target tissue 101 inside a body cavity using this endoscope. This embodiment shows an example in which target tissue 101 is the stomach (denoted as "stomach 101" hereinafter), and explains a method for transferring the stomach 101 inside the body and a treatment method for the upper stomach. Specifically, this embodiment relates to a method for securing space inside the body that is required in order to perform incising and suturing of the esophagus 102 and the stomach 101 in a Heller-Dor surgery. Heller-Dor is a technique for treating esophageal achalasia which occurs when there is a narrowing of the esophagus due to mechanical injury to the lower esophageal sphincter, and is for relieving esophageal obstruction by cutting the muscular layer of the esophagus 102, and preventing reflux from the stomach 101 to the esophagus 102 by suturing a portion of the stomach 101 to the esophagus 102. Namely, target site T which is to be treated is on target tissue 101, and is located at the lower esophago-cardiac area 102A and the gastric fundus 103 in this embodiment.

As shown in FIG. 1, in human beings, the lower esophago-cardiac area 102A and the gastric fundus 103 are positioned toward the backside of the liver 105. For this reason, in order to carry out a procedure on the lower esophago-cardiac area 102A and the gastric fundus 103, a space must be created between the liver 105 and the stomach 101 by moving the liver 105 or the stomach 101 within the body. In some cases, the body position of the patient is varied, lowering the head in order to retract the liver 105 away from the vicinity of the stomach 101. However, in this case, because the liver and stomach are further closely adhered, it is necessary to open a small space between the liver 105 and the stomach 101 by transferring the stomach 101 inside the body.

In this embodiment, the example explained is one in which the lower esophago-cardiac area 102A and the gastric fundus 103 are pulled out to a position where they do not overlap the liver 105 by transferring the stomach 101 relative to the liver 105 in the direction of the patient's feet, so that the procedure can be carried out to the target site T.

Next, the instruments used in the biological tissue transfer method and biological tissue treatment method according to the present embodiment will be explained with reference to FIGS. 2A, 2B, 2C, 3A and 3B.

Figure 2A:
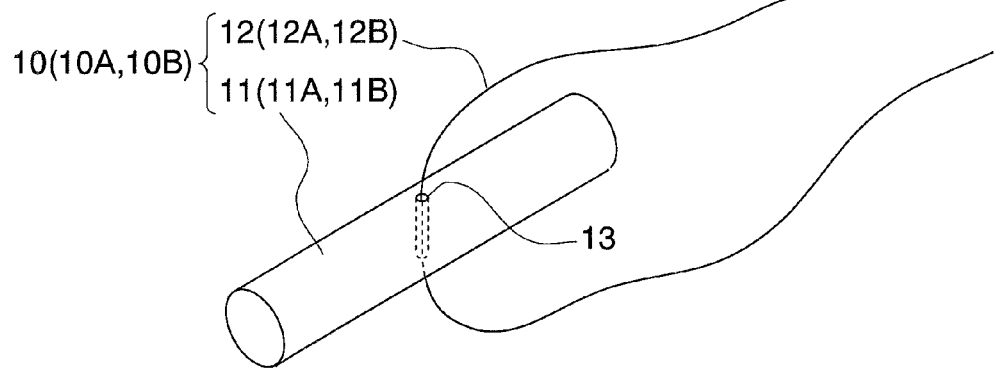
FIG. 2A is a perspective view showing the traction member used in the same biological tissue transfer method.
Figure 2B:
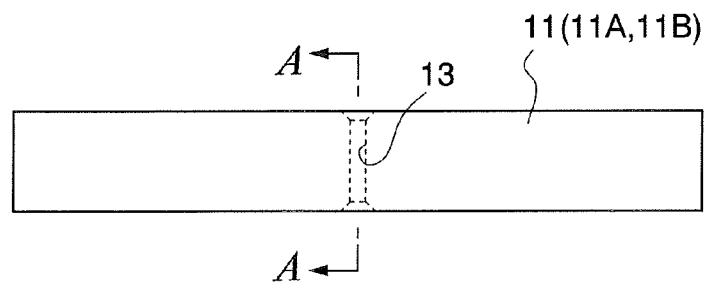
FIG. 2B is a planar view showing the structure of the rod in the same traction member.
Figure 2C:
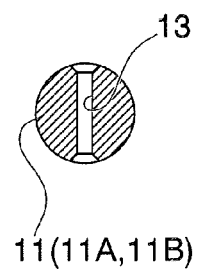
FIG. 2C is a cross-sectional view along the line A-A in FIG. 2B.

FIG. 2A is a perspective view showing the traction member 10 used in the biological tissue transfer method according to the present embodiment. FIG. 2B is a planar view showing the structure of the rod 11 in the traction member 10. FIG. 2C is a cross-sectional view along the line A-A in FIG. 2B. FIG. 3A is a cross-sectional view showing the structure of an indwelling implement 20 for fixing the traction member 10 in the target tissue 101. FIG. 3B is a view for explaining the action during use of the indwelling implement 20.

As shown in FIG. 2A, traction member 10, which is employed to place traction on stomach 101, is provided with a cylindrically shaped rod 11 in which a through hole 13 is formed through the center along the axial direction, and a traction suture 12, which is inserted and passed through the through hole 13 in the rod 11.

As shown in FIGS. 2B and 2C, the rod 11 of the traction member 10 has an axial length of 1 to 2 cm for example, and is formed to have a size which can be naturally expelled to the outside of the body via the gastrointestinal tract. The diameter of the rod 11 is a least greater than the diameter of the traction suture 12 since a through hole 13 for passing the traction suture 12 must be formed in the rod 11. In addition, the diameter of the rod 11 is suitably determined after taking into consideration that the rod 11 must possess a degree of rigidity sufficient to prevent bending thereof during use, while at the same time providing for minimizing of the size of the penetrating hole which is formed in the body wall for introducing the rod 11 into the body cavity.

In this embodiment, the through hole 13 formed in the rod 11 is formed to extend in the direction perpendicular to the center axis of the rod 11, and has a tapered edge at the opening of the through hole 13. As a result, it is possible to prevent catching or cutting of the traction suture 12 on the edge of the opening.

The traction suture 12 of the traction member 10 must consist of biologically suitable material.

As shown in FIG. 3A, the indwelling implement 20 consists of a tubular piercing needle 21 having a distal end 21A which is formed to be sharp, and a plunger 22 which is inserted from the proximal end 21B of the piercing needle 21 into the piercing needle 21. The piercing needle 21 has an inner diameter that can hold the rod 11 internally, and is formed to have a cylindrical shape which maintains a rigidity sufficient to prevent bending within the body cavity. The distal end of the piercing needle 21 is formed to be sufficiently sharp to form a penetrating hole in the body wall. The piercing needle 21 can be inserted through the body wall, with the distal end inserted into the body cavity. In addition, in this embodiment, the piercing needle 21 can be inserted through the stomach wall, with the distal end of the piercing needle 21 introduced inside the stomach 101.

The indwelling implement 20 is prepared prior to the procedure and is arranged so that the rod 11 is disposed to the distal end side of the plunger 22 inside the piercing needle 21, and the traction suture 12 is pulled out from the proximal end of the piercing needle 21. The rod 11 can be prevented from falling off the distal end of the piercing needle 21 by pulling the traction suture 12 out from the proximal end of the piercing needle 21. Note that it is not essential to pull the traction suture 12 out from the proximal end of the piercing needle 21.

As shown in FIG. 3B, when the plunger 22 is shifted to the distal end side of the piercing needle 21, the rod 11 is pressed by the distal end of the plunger 22 and is pushed out from the distal end of the piercing needle 21.

Note that the design of the indwelling implement 20 is not limited to that described above. Rather, any design is acceptable provided that it is one in which the traction member 10 can be introduced into the body cavity by passing through the body wall.

The technique for transferring the stomach 101 within the body using the traction member 10 and the indwelling implement 20 and carrying out a treatment on the stomach 101 and the esophagus 102 will now be explained with reference to FIGS. 4 through 17.

In the present embodiment, two traction members 10 are employed to transfer the stomach 101 inside the body. These two traction members 10 will be distinguished from one another by designating as "first traction member 10A" and "second traction member 10B". Rod 11 and traction suture 12 will be similarly denoted as "first rod 11A" and "second rod 11B", and "first traction suture 12A" and "second traction suture 12B".

Figure 5:
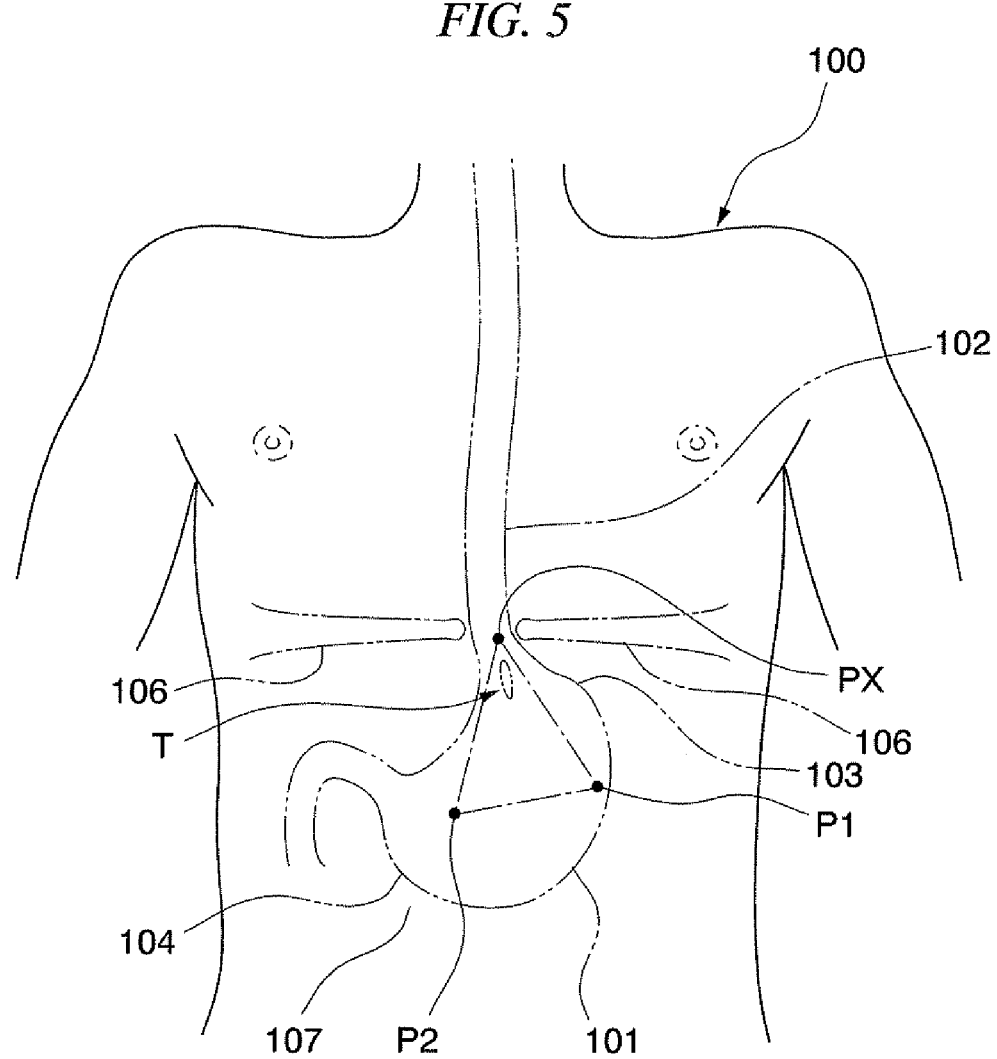
FIG. 5 is a schematic view for explaining the same biological tissue transfer method, and the biological tissue treatment method using this same biological tissue transfer method, showing the abdomen of the patient to be treated.

FIG. 4 is a flow chart for explaining the steps in the biological tissue transfer method and the biological tissue treatment method employing the biological tissue transfer method according to the present embodiment. FIG. 5 is a schematic view for explaining the biological tissue transfer method and the biological tissue treatment method using this biological tissue transfer method, and shows the abdomen of the patient 100 to be treated.

First, the position for attaching the first traction member 10A and the second traction member 10B to the stomach 101 is determined. In this embodiment, the position for attaching the first traction member 10A and the second traction member 10B to the stomach 101 are the two sites designated as "first position P1" on the gastric fundus 103 side and "second position P2" on the pylorus 104 side. Positions suitable for the first position P1 and the second position P2 are sites which will form the points of a triangle surrounding the target site T, in which the three points of the triangle consist of the second position P2, the first position P1 and the position of the esophageal hiatus, where the lower part of the esophagus passes 102 through the thoracic diaphragm 106 (this position denoted as "connecting position PX" where the esophagus 102 connects with the thoracic diaphragm 106 and at which the esophagus 102 is supported). Note that the stomach 101 may be visualized using ultrasound or the like to respectively determine the first position P1 and the second position P2.

Next, the first traction member attaching step S1 (see FIG. 4), for attaching the first traction member 10A to the first position P1 of the stomach 101, is carried out.

Figure 6:
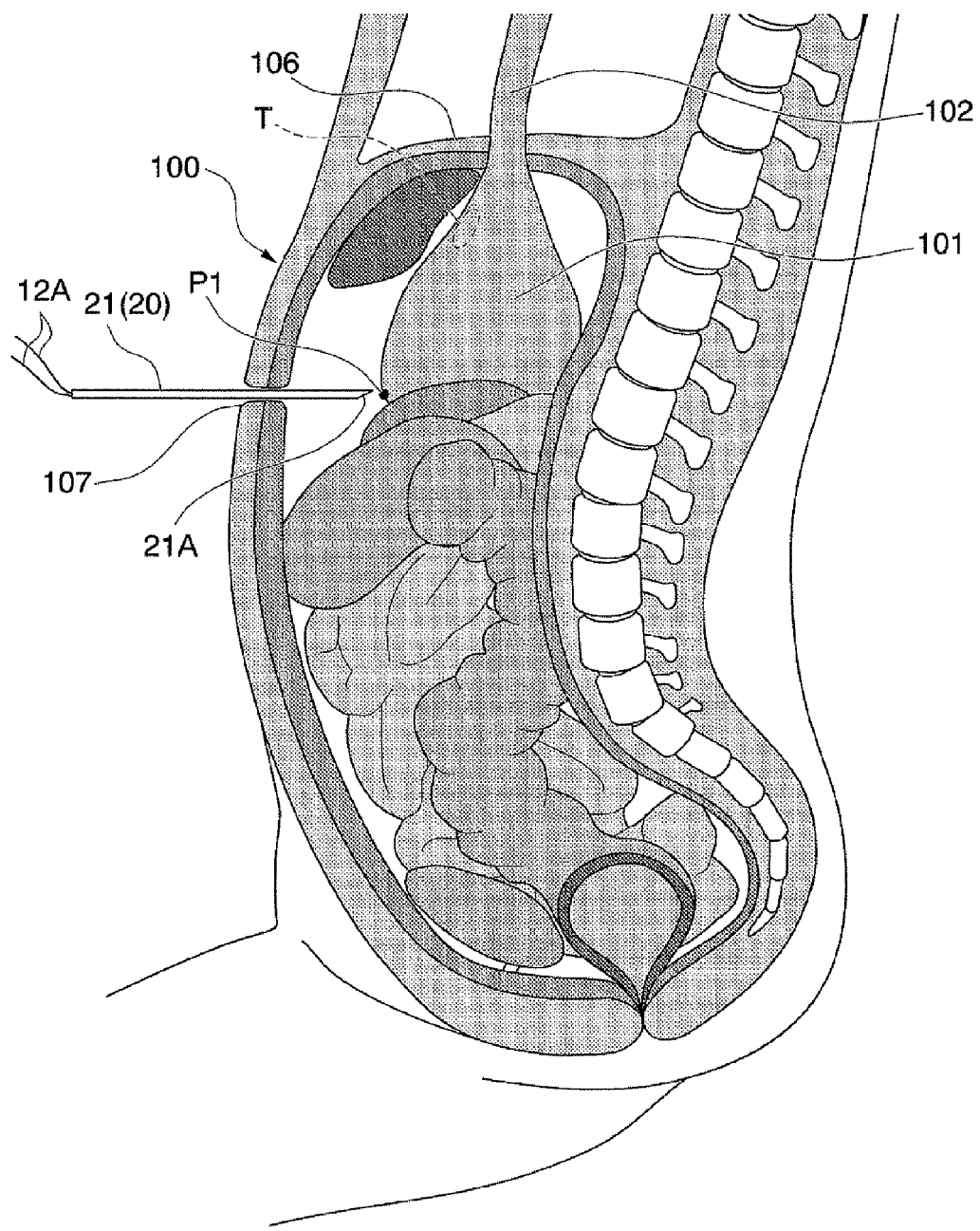
FIG. 6 is a schematic view for explaining the same treatment method, and shows the right half of the body of the patient in cross-section along the sagittal plane of the patient.
Figure 7:
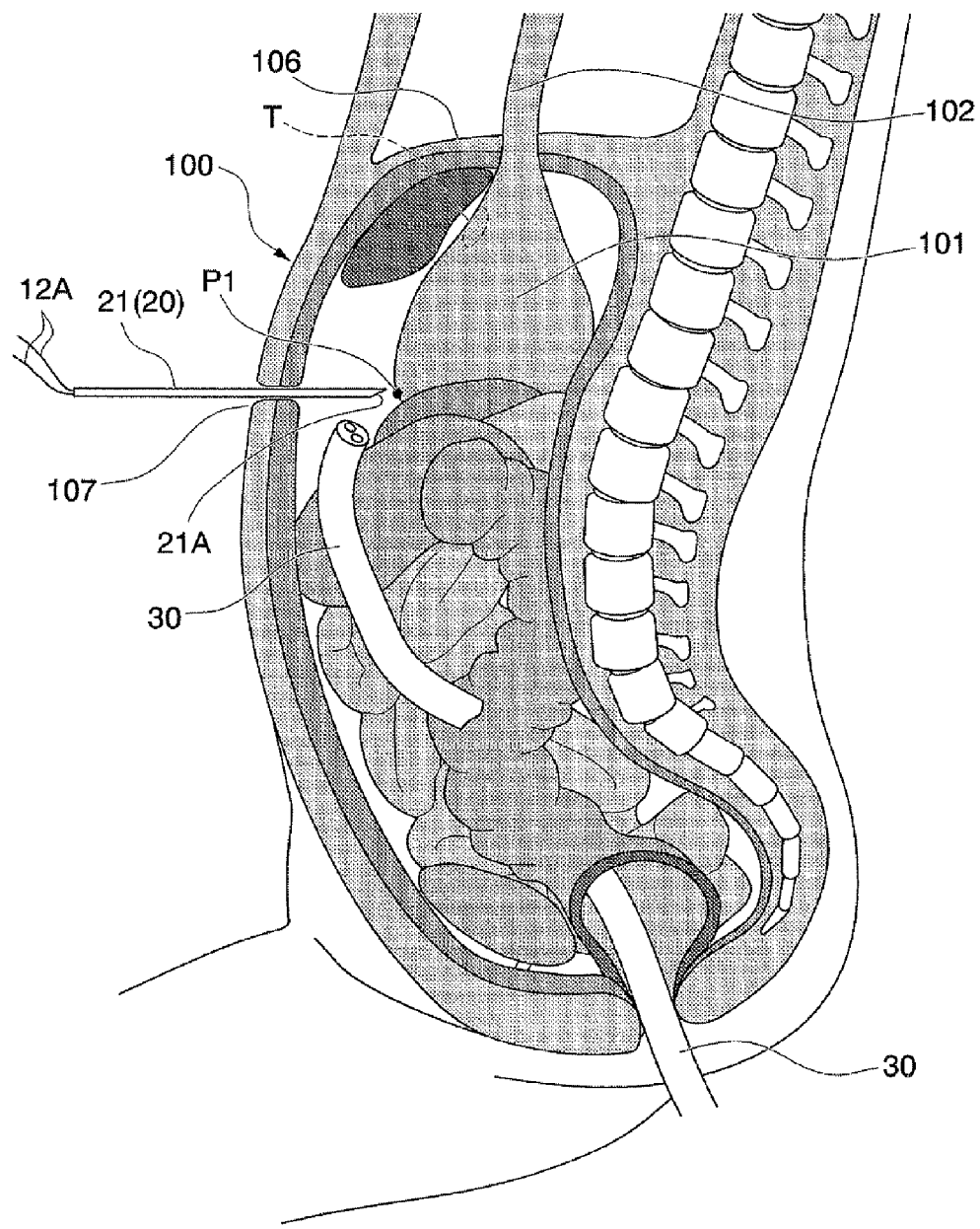
FIG. 7 is a schematic view for explaining the same treatment method, and shows the right half of the body of the patient in cross-section along the sagittal plane of the patient.

FIG. 6 is a schematic view for explaining the biological tissue treatment method. FIG. 6 is a view showing the right half of the body of the patient 100 in cross-section along the sagittal plane of the patient 100. FIG. 7 is a schematic view for explaining the biological tissue treatment method, and shows the right half of the body of the patient 100 in cross-section along the sagittal plane of the patient 100.

In the first traction member attaching step S1, a piercing needle 21 is used to pierce the abdomen of the patient 100 beginning with its distal end 21A, so as to pass through the body wall 107, as shown in FIG. 6. The piercing needle 21 is then pushed into the stomach 101 from the first position P1 of the stomach 101. When pushing the piercing needle 21 into the stomach 101, it is acceptable to employ an ultrasonic image or the like to visually confirm the position of the stomach 101. In addition, in order to accurately pierce the first position P1 with the piercing needle 21 inside the body cavity, it is also acceptable for the user to insert an endoscope 30 into the intestine of the patient 100 via the anus, and then pass this endoscope 30 through the intestinal wall so that it is introduced within the body cavity, as shown in FIG. 7. With this arrangement in place, the user can pierce the first position P1 with the piercing needle 71 while visualizing the stomach 101. In this case, it is preferable to create a space for introducing the endoscope 30 by introducing a gas into the abdominal cavity via the endoscope 30.

Once the distal end 21A of the piercing needle 21 has been introduced inside the stomach 101, the plunger 22 is pushed toward the distal end side of the piercing needle 21 as shown in FIG. 3B, and the first rod 11A is pushed out from the end of the piercing needle 21 within the stomach 101. So that the first traction suture 12A which is pulled out from the proximal end of the piercing needle 21 does not become completely pulled inside the piercing needle 21, the user holds down the first traction suture 12A at this time. Next, the user pulls the piercing needle 21 out from the stomach wall. Once the distal end of the piercing needle 21 is pulled out from the stomach wall, the user pulls the piercing needle 21 out from the abdominal wall 107 while leaving a portion of the first traction suture 12A within the body cavity. As a result, part of the first traction suture 12A and the first rod 11A are disposed inside the stomach 101, the other part of the first traction suture 12A is disposed to the outside of the stomach 101 inside the body cavity, and the part near the ends of the first traction suture 12A are disposed to the outside of the abdominal wall from the abdominal wall penetration point of the piercing needle 21 (see FIG. 8A).

This concludes the first traction member attaching step S1, and the procedure progresses to the second traction member attaching step S2 (see FIG. 4).

In the second traction member attaching step S2, as in the case of the above-described first traction member attaching step S1, the piercing needle 21 is pushed into the abdomen of the patient 100 from its distal end so as to penetrate the abdominal wall 107. The piercing needle 21 is pushed into the stomach 101 from the second position P2 of the stomach 101 (see FIG. 5), and part of the second traction suture 12B and the second rod 11B are disposed inside the stomach 101. The other part of the traction suture 12 is disposed outside the stomach 101 inside the body cavity, and the piercing needle 21 is pulled out from the body wall. As a result, the parts near the ends of the second traction suture 12B are disposed outside the abdominal wall from the abdominal wall penetration point of the piercing needle 21.

Figure 8A:
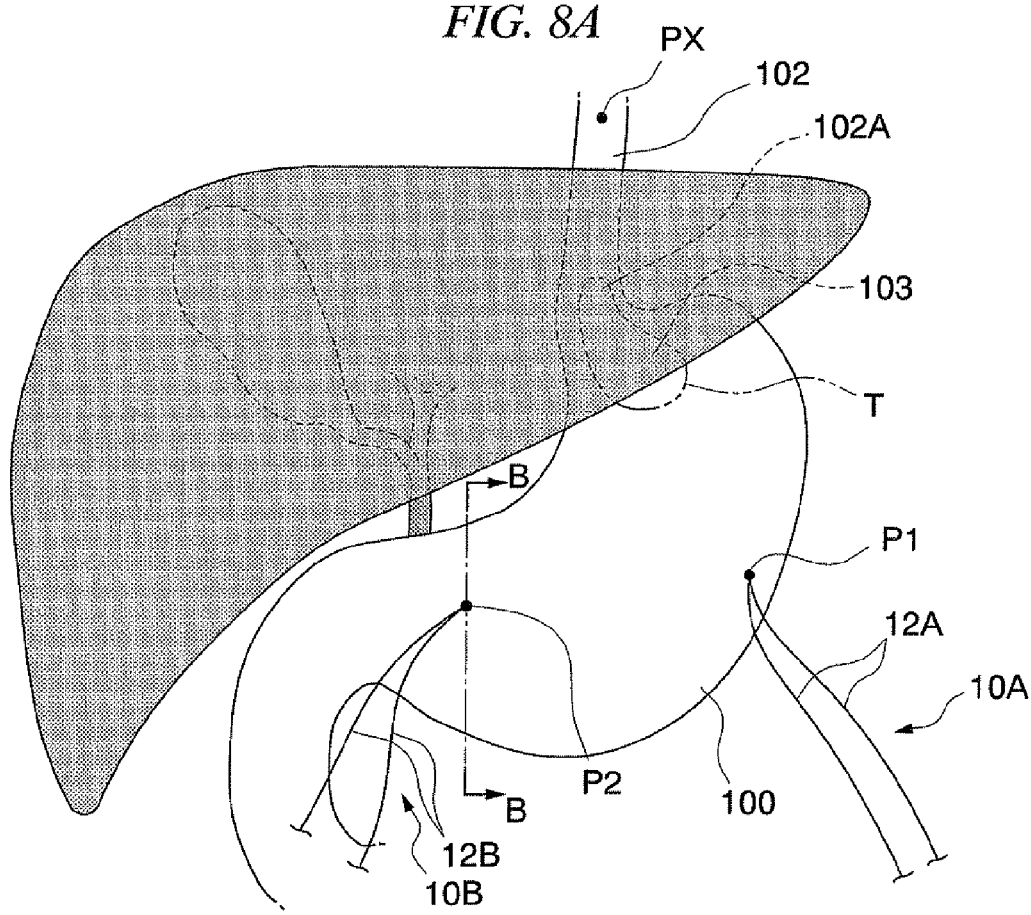
FIG. 8A is a view showing the one step in the same treatment method, and is a schematic anatomical diagram showing the abdomen of a patient on which the treatment method is to be performed.
Figure 8B:
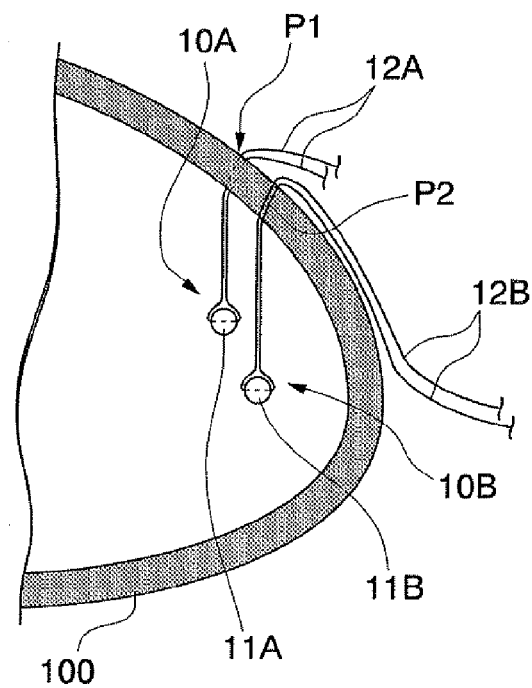
FIG. 8B is a cross-sectional view along the line B-B in FIG. 8A, and is a schematic view showing the arrangement when the first traction member and the second traction member are attached to the stomach.

FIG. 8A is a view showing one step in the biological tissue treatment method, and is a schematic anatomical diagram showing the abdomen of the patient 100 to be treated. FIG. 8B is a cross-sectional view along the line B-B in FIG. 8A, and is a schematic view showing an arrangement in which the first traction member 10A and the second traction member 10B are attached to the stomach 101.

As shown in FIG. 8A, the traction sutures 12 pass through the stomach wall and are pulled to the outside of the stomach 101 at the respective first position P1 and second position P2. As shown in FIG. 8B, the first rod 11A and the second rod 11B serve as respective anchors inside the stomach 101 to prevent the first traction suture 12A and the second traction suture 12B from falling out respectively from the stomach 101.

Note that as long as a load sufficient to bend and break the piercing needle 21 which has been passed through the body wall is not applied to the piercing needle 21, then, for example, it is possible to attach both the first traction member 10A and the second traction member 10B to the piercing needle 21, and to attach both the first traction member 10A and the second traction member 10B to the first position P1 and the second position P2 with a single piercing. The stress on the patient is thus reduced in this case, since the patient is only pierced by the needle once.

This concludes the second traction member attaching step S2, and the procedure progresses to the withdrawing step S3 (see FIG. 4).

The withdrawing step S3 is a step for extending the first traction suture 12A and the second traction suture 12B attached respectively at the first position P1 and the second position P2 inside the stomach 101 and for withdrawing the first traction suture 12A and the second traction suture 12B through the abdominal wall 107 to the outside of the body. In this withdrawing step S3, the positions of penetrating holes (withdrawal positions P3,P4), which are formed in the body wall for pulling the first traction suture 12A and the second traction suture 12B out through the body wall, are first determined. In the withdrawing step S3, as shown in FIG. 9 when viewed perpendicular to the front surface of the patient, withdrawal position P3 is set to a site which is farther from the connecting position PX than the first position P1 on a straight line L1 which passes through the connecting position PX and the first position P1, and withdrawal position P4 is set to a position which is further from the connecting position PX than the second position P2 on a straight line L2 passing through the connecting position PX and the second position P2.

Figure 9:
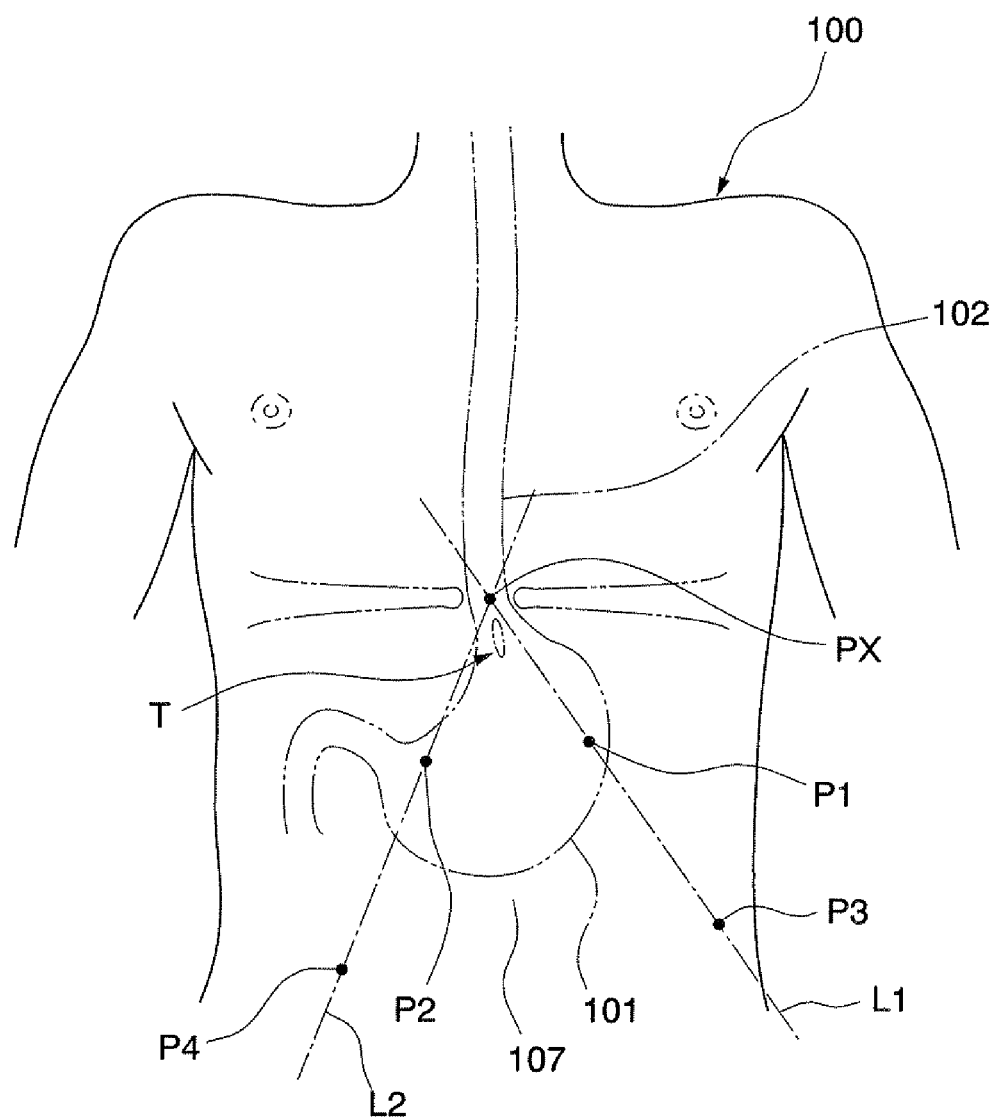
FIG. 9 is a view showing one step in the same treatment method, and shows the position of the penetrating hole that is formed in the body wall for pulling the first traction member and the second traction member to the outside of the body.

Preferably, as shown in FIG. 9, in the withdrawing step S3, the position at which a straight line extending from the connecting position PX toward the first position P1 intersects with the abdominal wall 107, and the position at which a straight line extending from the connecting position PX toward the second position P2 intersects with the abdominal wall 107, are defined as withdrawal positions P3,P4 respectively. In this case, the material comprising the first traction member 10A and the second traction member 10B may be one which can be confirmed via radiographic imaging, or a marker that can be confirmed radiographically may be provided in advance to the first traction member 10A and the second traction member 10B. As a result, it is possible to easily set the withdrawal positions P3,P4 after confirming the positions of the first traction member 10A and the second traction member 10B within the body cavity.

Figure 10:
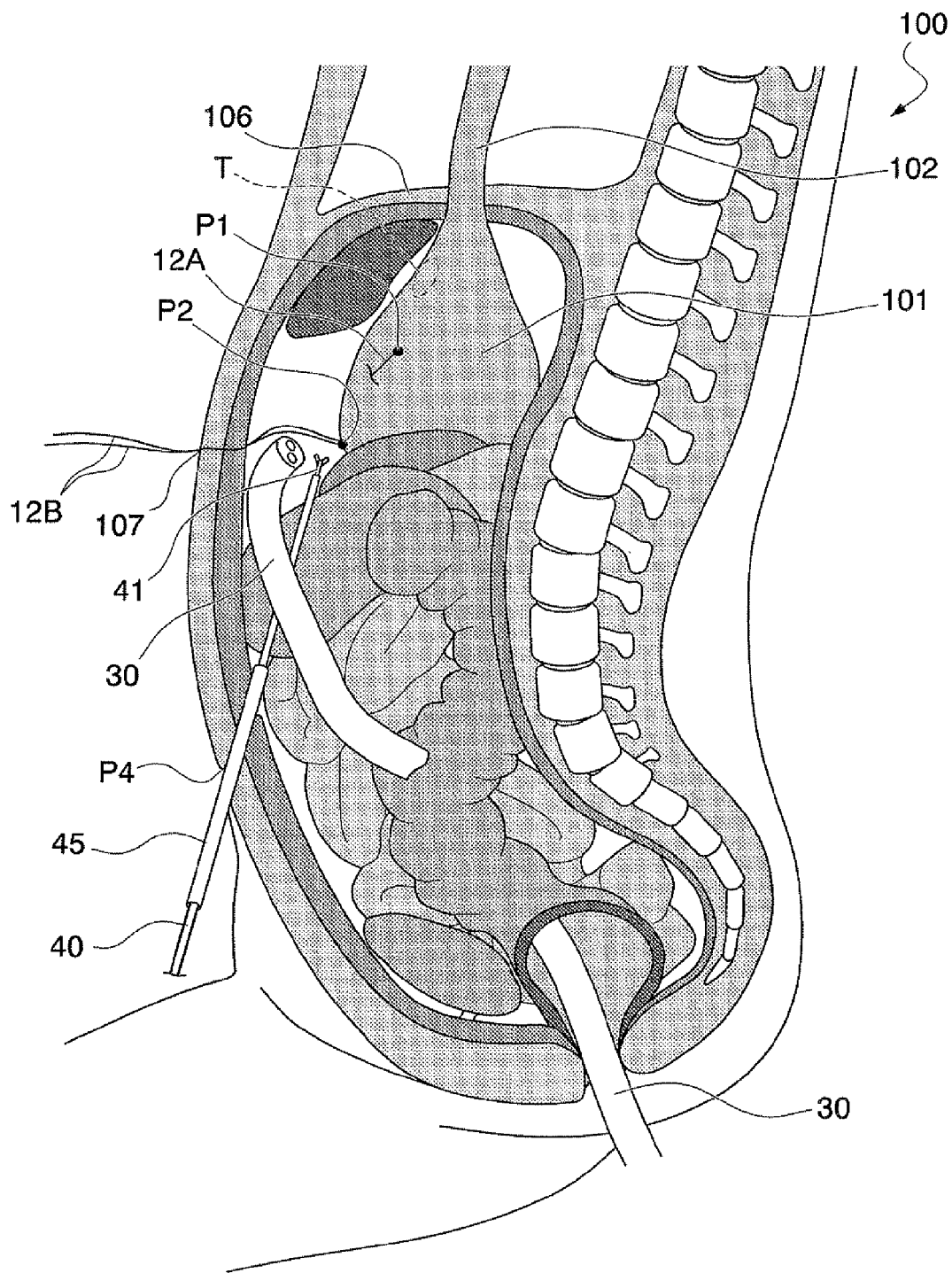
FIG. 10 is a view showing one step in the same treatment method, and is for explaining the action of the laparoscopic forceps for pulling the second traction member which is attached to the target tissue to the outside of the body.
Figure 11:
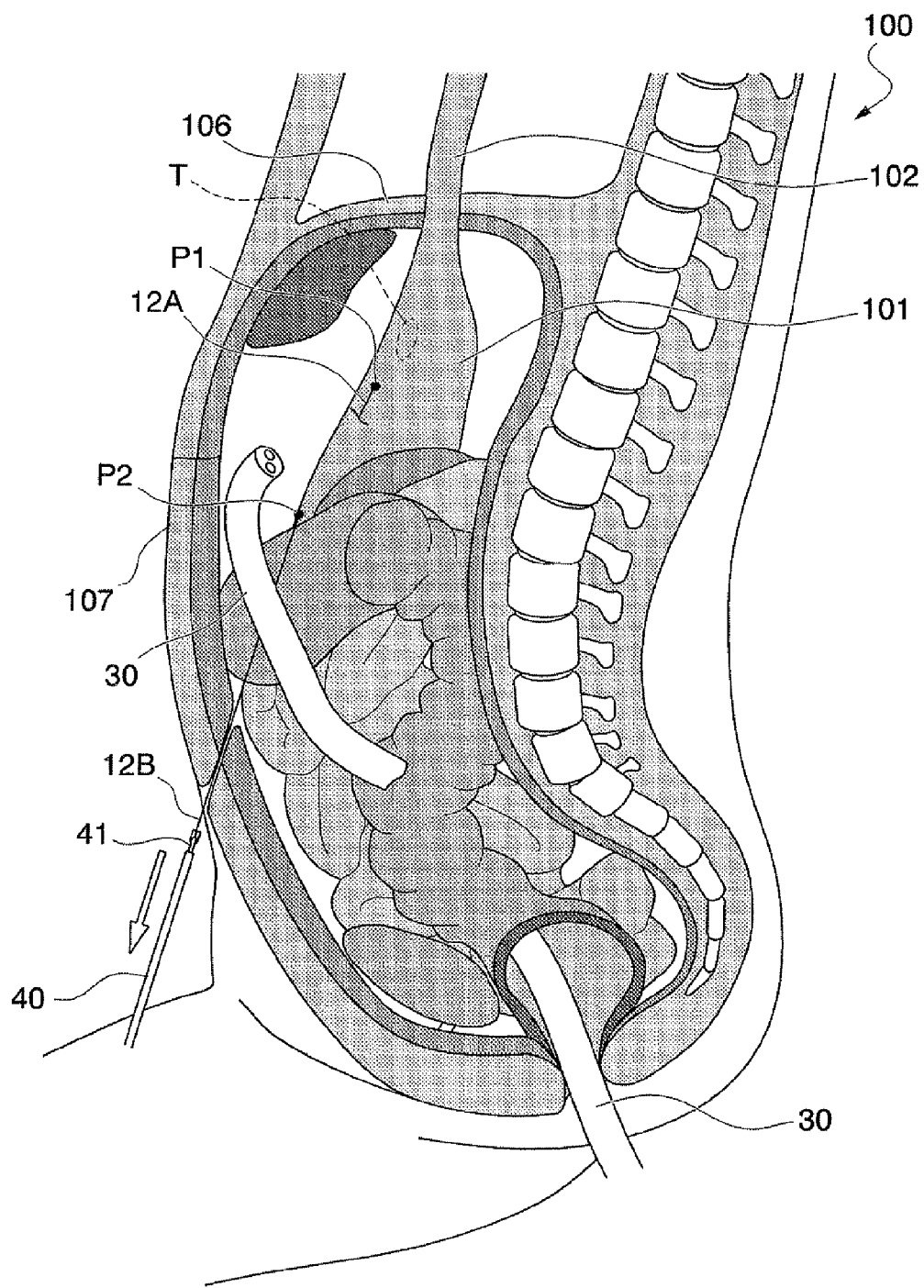
FIG. 11 is a view showing one step in the same treatment method, and is for explaining the action to pull the second traction member which is attached to the target tissue to the outside of the body.

FIG. 9 shows one step in the biological tissue treatment method, and shows the position of the penetrating hole formed in the body wall for withdrawing the first traction member 10A and the second traction member 10B to the outside of the body. FIG. 10 shows one step in the biological tissue treatment method, and is for explaining the action of the forceps for withdrawing the second traction member 10B which is attached to the target tissue 101 to the outside of the body. FIG. 11 shows one step in the biological tissue treatment method, and is for explaining the action to withdraw the second traction member 10B which is attached to the target tissue 101 to the outside of the body.

Next, a penetrating hole is made at respective withdrawal positions P3,P4 shown in FIG. 9, using an indwelling needle equipped with a catheter 45 and an inner needle (not shown) that is housed inside the catheter 45. The inner needle is withdrawn to leave behind the catheter 45 of the indwelling implement. As shown in FIG. 10, laparoscopic forceps 40, which have a grasping part 41 for grasping the first traction suture 12A and the second traction suture 12B are introduced into the body cavity by passing through the catheter 45 which is disposed at the withdrawal positions P3,P4 (FIG. 10 shows the arrangement when the laparoscopic forceps 40 are introduced from the withdrawal position P4 in order to carry out the withdrawing step S3 to the second traction suture 12B).

Note that in the case where an endoscope 30 is not introduced into the body cavity in the first traction member attaching step S1 and the second traction member attaching step S2, the endoscope 30 is introduced into the body cavity as described above prior to introducing the laparoscopic forceps 40 into the body cavity. As shown in FIG. 10, the user visually confirms the position of the grasping part 41 of the laparoscopic forceps 40 using the endoscope 30 described above, and uses the grasping part 41 to grasps the second traction suture 12B which is outside the stomach 101. Next, the user moves the laparoscopic forceps 40 which are grasping the second traction suture 12B toward the withdrawal position P4 side. By winding the traction suture several times, both ends of the second traction suture 12B which are sticking out from the point of abdominal wall penetration of the piercing needle 21 are introduced into the body cavity. Note that when this manipulation is difficult, the field of view of the endoscope 30 is improved by inserting the laparoscopic forceps 40 from the withdrawal position P3, thus facilitating the action. When withdrawing the first traction suture 12A, the approach does not change because a penetrating hole is provided at the withdrawal position P3 as well.

In addition, as shown in FIG. 11, with the second traction suture 12B grasped by the laparoscopic forceps 40 which have been inserted from the withdrawal position P4, the laparoscopic forceps 40 and the catheter 45 are pulled out from the body wall, and the second traction suture 12B is pulled out from the withdrawal position P4 to the outside of the body. As a result, the second traction suture 12B extends from the connecting position PX toward the second position P2 side. In this embodiment, the center of the second traction suture 12B is left inside the stomach 101, and the ends of the second traction suture 12B are pulled to the outside of the body. Note that while detailed views are omitted, the withdrawing step S3 for first traction suture 12A and the withdrawing step S3 for second traction suture 12B are carried out similarly, with the first traction suture 12A extending from the connecting position PX to the first position P1 side.

This concludes the withdrawing step S3, and the procedure progresses to the transferring step S4 (see FIG. 4).

Figure 12:
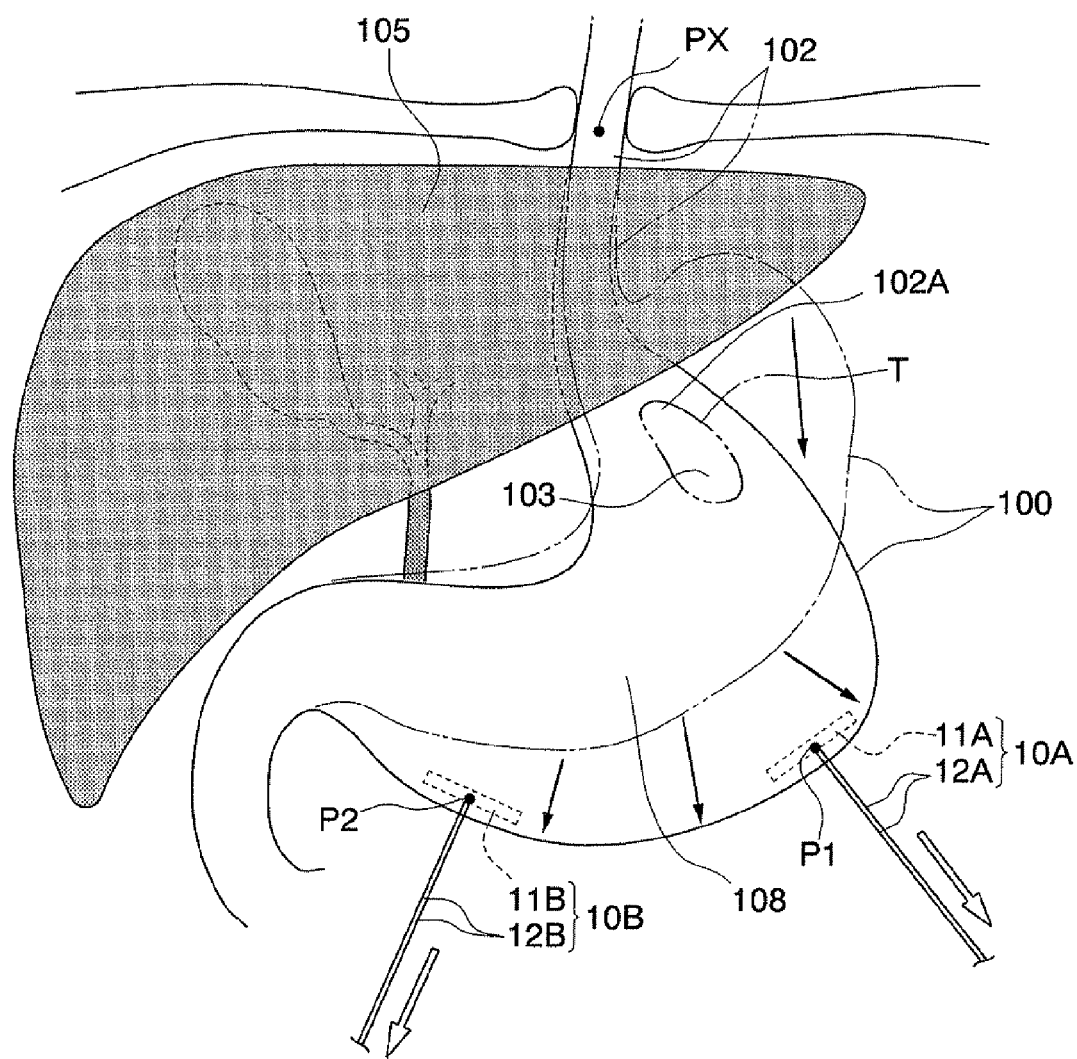
FIG. 12 is a view showing one step in the same treatment method, and is for explaining the action for transferring the stomach within the body using the first traction member and the second traction member.

The transferring step S4 is a step in which the target tissue 101 is transferred by applying traction through manipulation by the user on the first traction suture 12A and the second traction suture 12B which were pulled to the outside of the body in the withdrawing step S3. FIG. 12 is a view showing one step in the biological tissue treatment method, and is for explaining the action for transferring the stomach 101 inside the body using the first traction member 10A and the second traction member 10B.

In the transferring step S4, traction directed toward the outside of the body is applied to the first traction suture 12A and the second traction suture 12B (see FIG. 11), which have been pulled to the outside of the body. As a result, as shown in FIG. 12, the first rod 11A and the second rod 11B which are disposed inside the stomach 101 are pulled respectively toward the withdrawal positions P3,P4 which are formed in the abdominal wall 107 (see FIG. 9), so that the first rod 11A and the second rod 11B come into contact with the stomach wall. When the user applies further traction on the first traction suture 12A and the second traction suture 12B, the stomach 101 is moved by the first rod 11A and the second rod 11B which are pulled by the first traction suture 12A and the second traction suture 12B respectively. As a result, the lower esophago-cardiac area 102A and the gastric fundus 103 are pulled out from under the liver 105. Further, the first traction suture 12A and the second traction suture 12B are pulled in directions which open the distance between the first position P1 and the second position P2, so that front wall 108 of the stomach deforms so that the surface area of the triangle consisting of the three points, i.e., connecting position PX, first position P1 and second position P2, widens. As a result, the target site T which includes a portion of the gastric fundus 103 and the lower esophago-cardiac area 102A flattens. Next, traction is applied to the stomach 101 in the direction of the traction on the first traction suture 12A and the second traction suture 12B. As a result, a space for treating the stomach 101 is generated on the front side thereof.

Figure 13A:
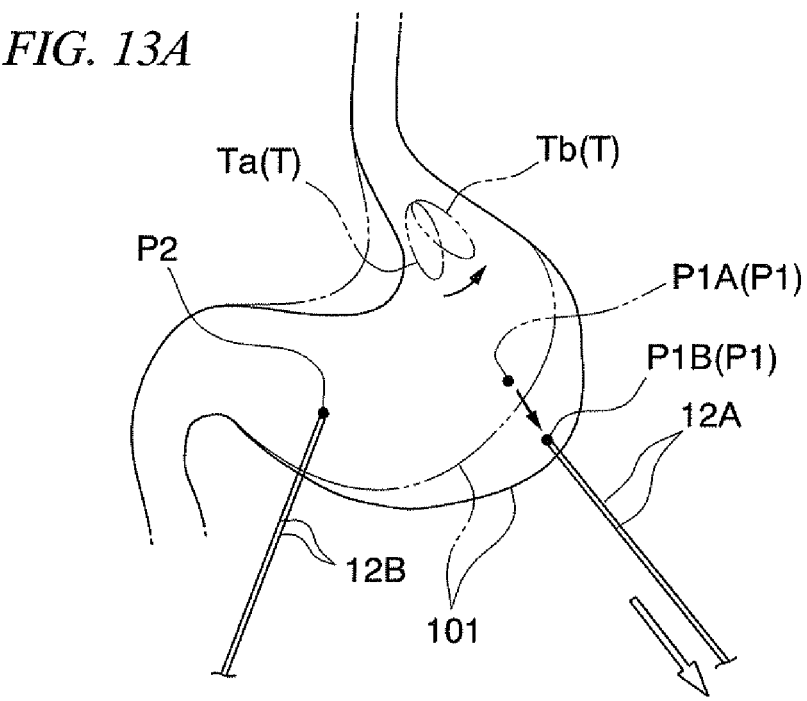
FIG. 13A and FIG. 13B are views showing one step in the same treatment method, and are for explaining the action for adjusting the inclination of the stomach using the first traction member and the second traction member.
Figure 13B:
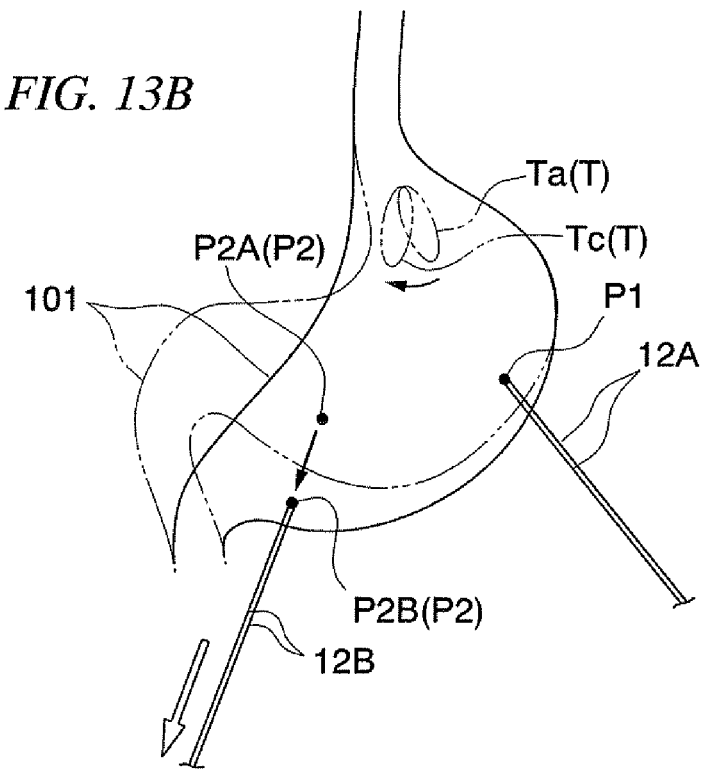

The stomach 101 can be transferred by varying the amount of traction on the first position P1 and the second position P2, respectively. For example, as shown in FIG. 13A, by pulling the stomach 101 from the position P1A to the position P1B at the first position P1 without applying traction on the stomach 101 on the second position P2 side, the stomach 101 is transferred to the left side of the patient 100. Conversely, as shown in FIG. 13B for example, by pulling the stomach 101 from the position P2A to the position P2B at the second position P2 without applying traction on the stomach 101 on the first position P1 side, the stomach 101 is transferred to the right side of the patient 100. In this way, by changing the amount of traction on first position P1 and second position P2 respectively, the first position P1 and the second position P2 side can be moved to the left or right employing connecting point PX as a pivot. As a result, as shown in FIG. 13A and FIG. 13B, the inclination of the target site T can be moved toward the left side of the patient 100 (from the direction indicated by the symbol Ta to the direction indicated by the symbol Tb in FIG. 13A), or toward the right side of the patient 100 (from the direction indicated by the symbol Ta to the direction indicated by the symbol Tc in FIG. 13B). In this way, the position of the stomach 101 can be adjusted so that the pre-determined incision line L (see FIG. 15) at which incision of the muscular layer of the lower esophago-cardiac area 102A is performed becomes a straight line in a direction that facilitates the approach by the treatment endoscope. This concludes the transferring step S4, and the procedure progresses to the treatment step S5.

Treatment step S5 is a step for treating the lower esophago-cardiac area 102A and the gastric fundus 103 which are the target sites T. In this embodiment, treatment step S5 is the step in which the Heller-Dor technique is performed.

Figure 14:
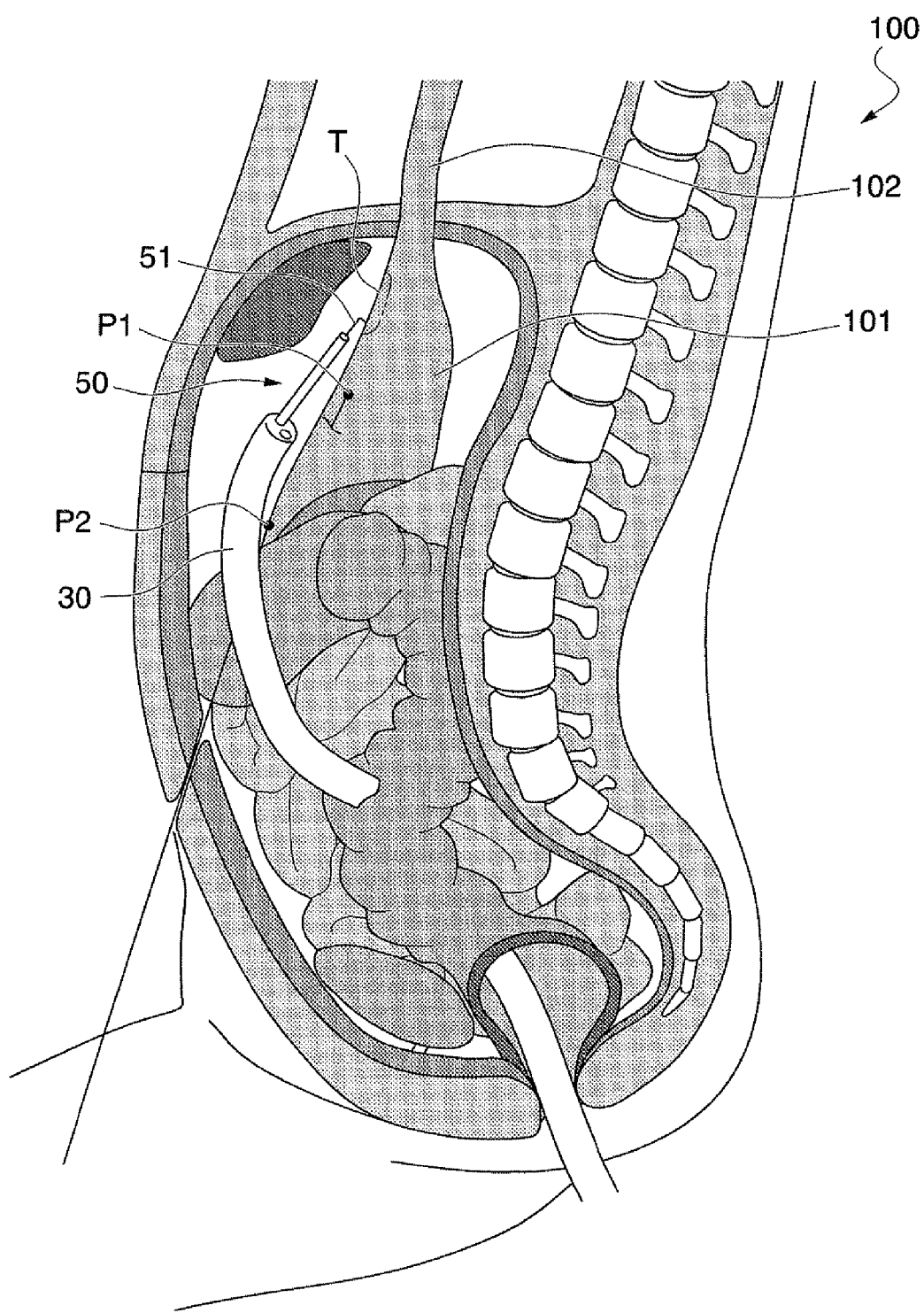
FIG. 14 is a view for explaining the action for guiding to the target tissue the indwelling implement which is for carrying out the procedure on the stomach after it has been transferred within the body.
Figure 15:
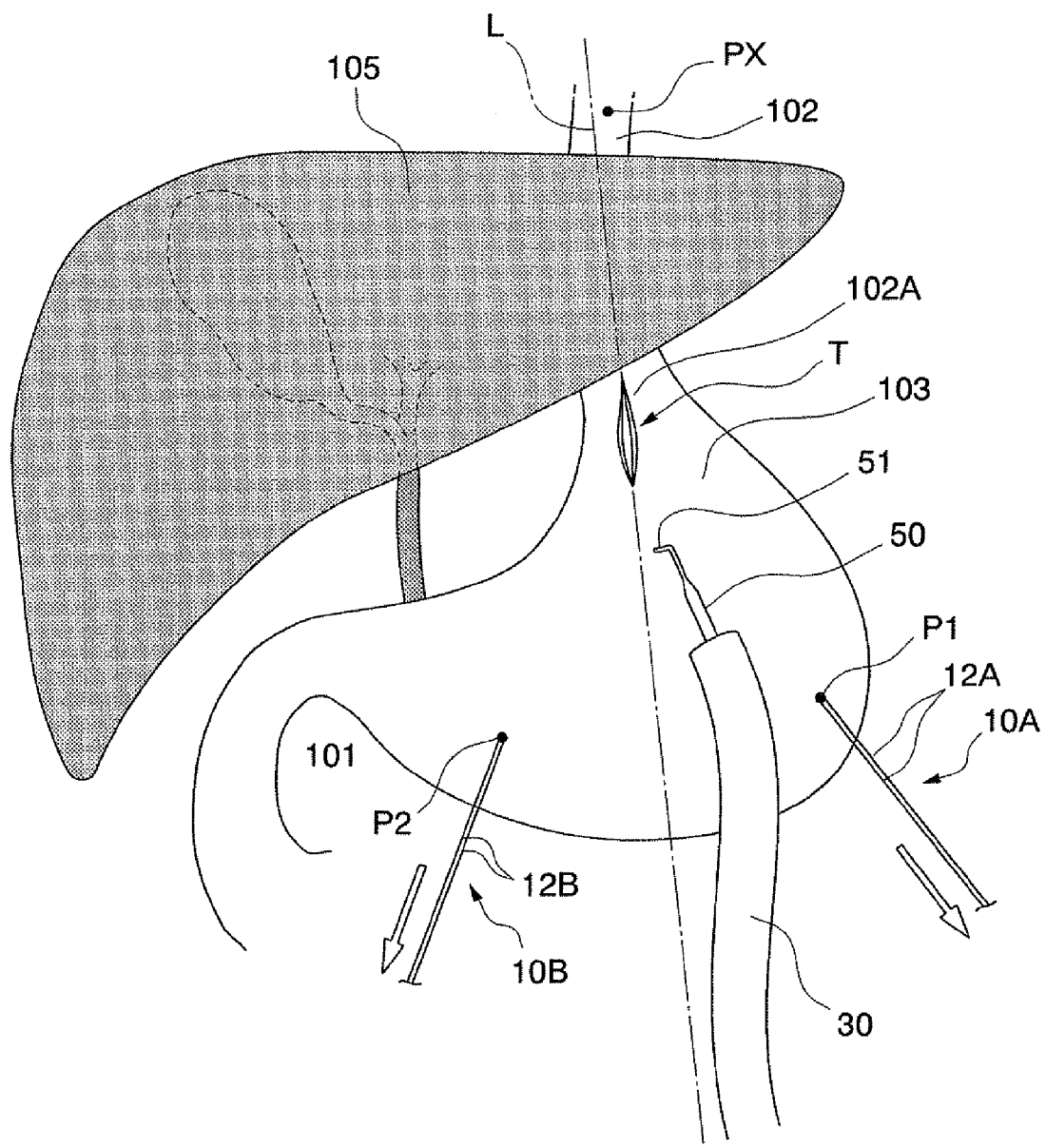
FIG. 15 is a view showing one step in the same treatment method, and is for explaining the action to incise the muscular layer of the esophagus.
Figure 16:
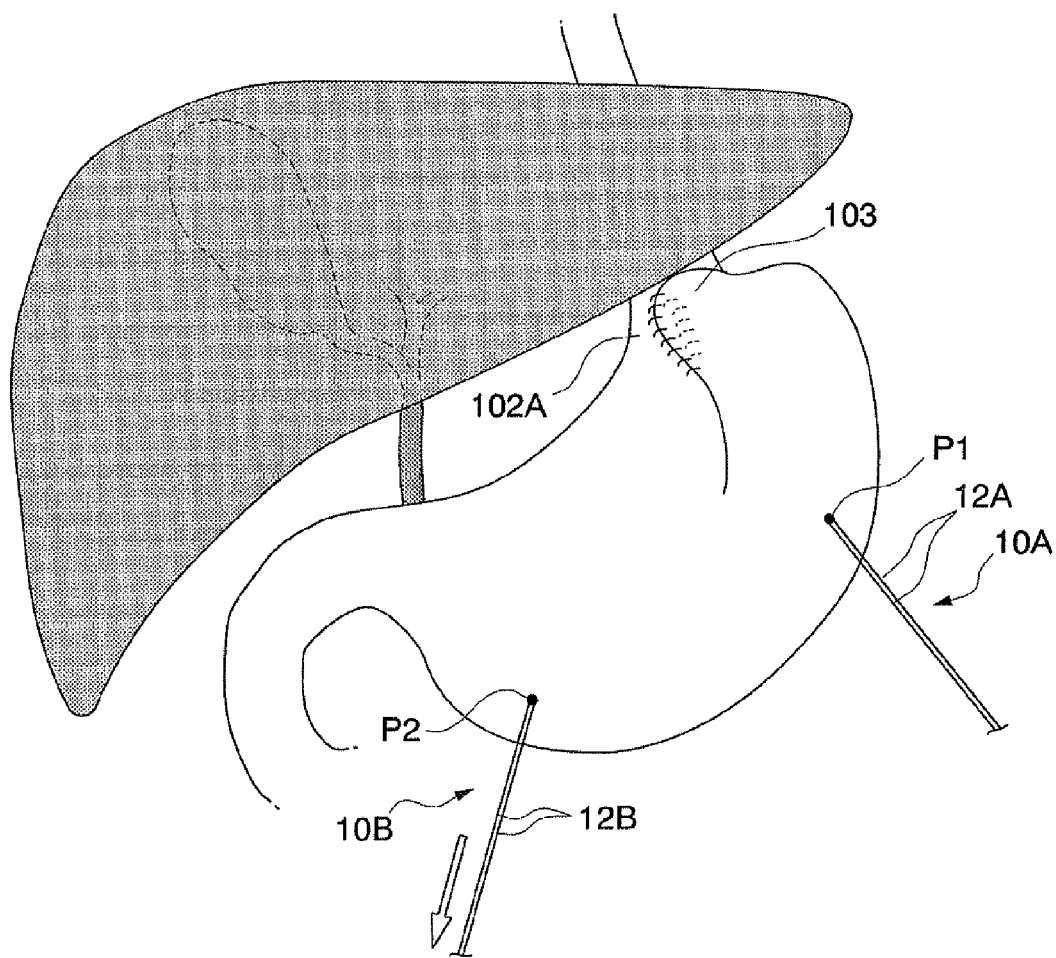
FIG. 16 is a view showing one step in the same treatment method, and shows the condition after completion of a gastric procedure using the Heller-Dor technique.
Figure 17:
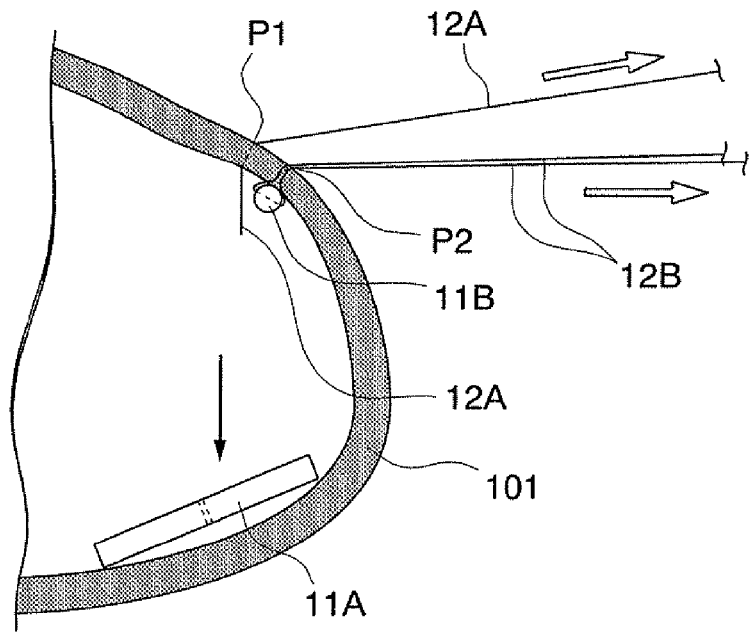
FIG. 17 is a view for explaining the action for releasing the first traction member from the target tissue after completion of the Heller-Dor technique.

FIG. 14 is a view for explaining the action in which an endoscope to perform a procedure on the stomach 101 is introduced into the body following once the stomach 101 has been transferred inside the body. FIG. 15 shows a step in the biological tissue treatment method, and is for explaining the action in which the muscular layer of the esophagus 102 is incised. Next, FIG. 16 shows a step in the biological tissue treatment method, and is a view showing the arrangement following completion of a procedure on the stomach 101 using the Heller-Dor technique. FIG. 17 is a view for explaining the action in which the first traction member 10A is released from the target tissue 101 after the conclusion of the Heller-Dor technique.

As shown in FIG. 14, in treatment step S5, the endoscopic cutting instrument 50 is passed through the endoscope 30 and guided to the target site T. In this embodiment, a hook-shaped cutting instrument having a hook 51 through which high frequency electrical current passes in order to perform cauterized cutting of biological tissue is employed as the endoscopic cutting instrument 50 for incising the muscular layer of the lower esophago-cardiac area 102A. Note that as needed it is also possible to use a forceps-shaped high-frequency endoscopic cutting instrument or endoscopic scissors which do not employ a high-frequency current.

As shown in FIG. 15, the user guides the hook 51 to the specific incision site by moving the endoscope 30 from between the first position P1 and the second position P2 toward the connecting position PX. In this embodiment, the stomach 101 is transferred using the first traction suture 12A and the second traction suture 12B, so that the endoscopic cutting instrument 50 can be guided to the lower esophago-cardiac area 102A which is the target site T without interfering with movement of the endoscope 30 or blocking the field of view.

Once the endoscopic cutting instrument 50 has been guided to the lower esophago-cardiac area 102A, the esophageal sphincter of the lower esophago-cardiac area 102A is incised as shown in FIG. 15. An explanation of details of the Heller-Dor technique is omitted here. However, the position of the stomach 101 is adjusted in the transferring step S4 so that the pre-determined incision line L for cutting the muscular layer of the lower esophgo-cardiac area 102A is straight and so that the inclination of the stomach 101 facilitates the approach of the endoscope 30, thus enabling easy cutting of the muscular layer. In addition, the position of the stomach 101 can be adjusted as necessary during the treatment step S5.

Once the muscular layer of the esophageal sphincter has been incised, a portion of the gastric fundus 103 is pulled over to the incised lower esophago-cardiac area 102A as shown in FIG. 16, and cardioplasty is performed by suturing together the incised area on the lower esohago-cardiac area 102A and the gastric fundus 103. Note that should excessive tension on the traction suture become problematic during the operation, the gastric fundus 103 may be transferred to the esophagus 102 side by relaxing traction on the traction suture.

Once suturing of the gastric fundus 103 is complete, traction on the first traction suture 12A and the second traction suture 12B at the first position P1 and the second position P2 is released. One of either the first traction suture 12A or the second traction suture 12B, the ends of which have been pulled out from the withdrawal positions P3,P4 (see FIG. 9), is pulled to the outside of the body. As shown in FIG. 17, when one end of the first traction suture 12A is pulled to the outside of the body, the first rod 11A falls free inside the stomach 101, and the first traction suture 12A can be pulled to the outside of the body while leaving the first rod 11A within the stomach 101. Likewise, the second traction suture 12B, which is attached at the second position P2, can similarly be pulled to the outside of the body. As a result, the first rod 11A and the second rod 11B are left behind within the stomach while all of the traction suture 12 is pulled outside the body. This concludes treatment step S5.

Note that the first rod 11A and the second rod 11B which remain inside the stomach 101 are passed from the stomach 101 to the intestines and expelled from the body via the anus.

It has been the conventional approach to carry out surgical procedures in a manner which reduces the stress on the patient by employing laparoscopes or treatment endoscopes which are passed through a natural orifice and introduced through the wall of a digestive organ. However, when the target site to be treated inside a body cavity is positioned at a location obscured by another tissue, then the other tissue must be retracted so that instruments and the like can be guided to the treatment site. However, in order to introduce a retractor for retracting the other tissue, it is necessary to form a separate penetrating hole in the abdominal and digestive organ walls. This is undesirable as there is a potential for increasing a burden on a patient. Moreover, disposing a retractor inside the body may complicate rotational manipulation of the endoscope in the restricted confines of the body cavity.

In contrast, in the biological tissue transfer method and the biological tissue treatment method according to this embodiment, the stomach 101 can be moved using the traction sutures 12, and the target site T can be pulled flat using traction sutures 12 in order to carry out cutting and suturing. As a result, an expanded space for rotating the endoscope 30 inside the body can be secured, and the stomach 101 can be maintained without hindering movement in the cutting direction when incising the muscular layer.

In addition, the traction member 10 which consists of the traction sutures 12 and the rod 11 can be inserted into the piercing needle 21, and attached to the stomach 101 by piercing the body wall and stomach wall with the piercing needle 21. As a result, it is not necessary to add a small incision in the body wall which would then have to be sutured after the procedure. Since there is almost no scar remaining, the burden on the patient 100 is reduced.

The position at which the piercing needle penetrates the abdominal wall can be provided directly above the traction suture attachment position. For this reason, the procedure is safe as other organs do not enter between the abdominal wall and the stomach wall, eliminating the danger of injuring another organ when performing the piercing operation and causing bleeding.

In addition, the laparoscopic forceps 40 are used when the traction suture is pulled to the outside of the body. However, since the function of the laparoscopic forceps is only to withdrawal the suture, the only force experienced by the forceps is in the longitudinal direction of the inserted part, and is not large. Thus, narrow diameter forceps on the order of, for example a diameter of 1.7 mm, may be used, these forceps being capable of insertion into the abdominal cavity through the indwelling catheter 45. There is no need to make an incision in the body wall, provide a trocar, or perform suturing after the procedure. Since there is almost no scar remaining, the stress on the patient 100 is reduced.

Further, because the rod 11 is attached to the traction suture 12, the traction force from the traction suture 12 is transferred to the stomach wall via the rod 11, preventing the traction suture 12 from digging into the stomach wall. As a result, stress to the stomach wall does not readily occur, even if a large amount of traction force is applied to the traction suture 12.

In addition, the rod 11 is cylindrical in shape and has a diameter larger than the traction suture 12. As a result, the surface are of contact between the rod 11 and the inner wall of the stomach 101 is greater than the contact surface area which exists if the traction suture 12 contacts the inner wall of the stomach 101. Accordingly, the possibility of damage to the stomach wall due to pressing of the rod 11 into the stomach wall is even further reduced.

Further, the traction suture 12 is passed through the through hole formed in the rod 11, and the ends of the traction suture 12 are pulled to the outside of the body with the middle portion of the traction suture 12 suspended on the rod 11. As a result, the rod 11 and the traction suture 12 can be connected with certainty and the rod 11 can be separated from the traction suture 12 by winding from the outside of the body as needed. As a result, it is easy to release the traction member 10 which is attached to the stomach 101 and to pull the traction suture 12 to the outside of the body within a short period of time without leaving any traction suture 12 behind in the body.

In addition, by applying traction on the traction sutures 12 at the first position P1 and the second position P2 respectively so as to change the distance (amount of traction) over which the stomach 101 is pulled, it is possible to adjust the position of the target site T so that the pre-determined incision line L becomes a straight line at the target site T where the incision is made. In particular, in the case of the area where cutting of the muscular layer is performed in the Heller-Dor technique, the pre-determined incision line has a curved form if the stomach 101 and esophagus 102 are not transferred. Thus, using the method according to the present embodiment provides for a linear pre-determined incision line L, so that the incising of the muscular layer can be carried out with greater precision.

Note that this embodiment disclosed an example in which the traction suture 12 which is disposed inside the body cavity is withdrawn to the outside of the body in withdrawing step S3. However, for example, when there is sufficient space within the abdominal cavity to permit disposition of endoscopic cutting instruments other than the endoscopic cutting instrument 50 for treating target site T, then it is acceptable to employ grasping forceps of the like, introduced into the body cavity via an endoscope, etc., to apply traction on the respective traction sutures 12 inside the abdominal cavity. In other words, in the withdrawing step S3, it is possible to apply traction to the traction sutures 12 inside the body without pulling the traction sutures 12 to the outside of the body. In this case, in the transferring step S4 which follows the withdrawing step S3, the target tissue 101 is transferred within the body by pulling on the traction sutures 12 through manipulations conducted via the endoscopic cutting instrument 50 of the endoscope 30, rather than through hand manipulations by the user. In this case, it is not necessary to make penetrating holes in the body wall for withdrawing the traction sutures 12 to the outside of the body. Thus, stress on the patient 100 is reduced.

Note that an example of using the Heller-Dor technique is explained in the treatment step S5 of the preceding embodiment. However, the present invention is not limited thereto. Other Fundoplication surgery technique may be used in the treatment step S5 instead of the Heller-Dor technique.

(Modifications)

Figure 18A:
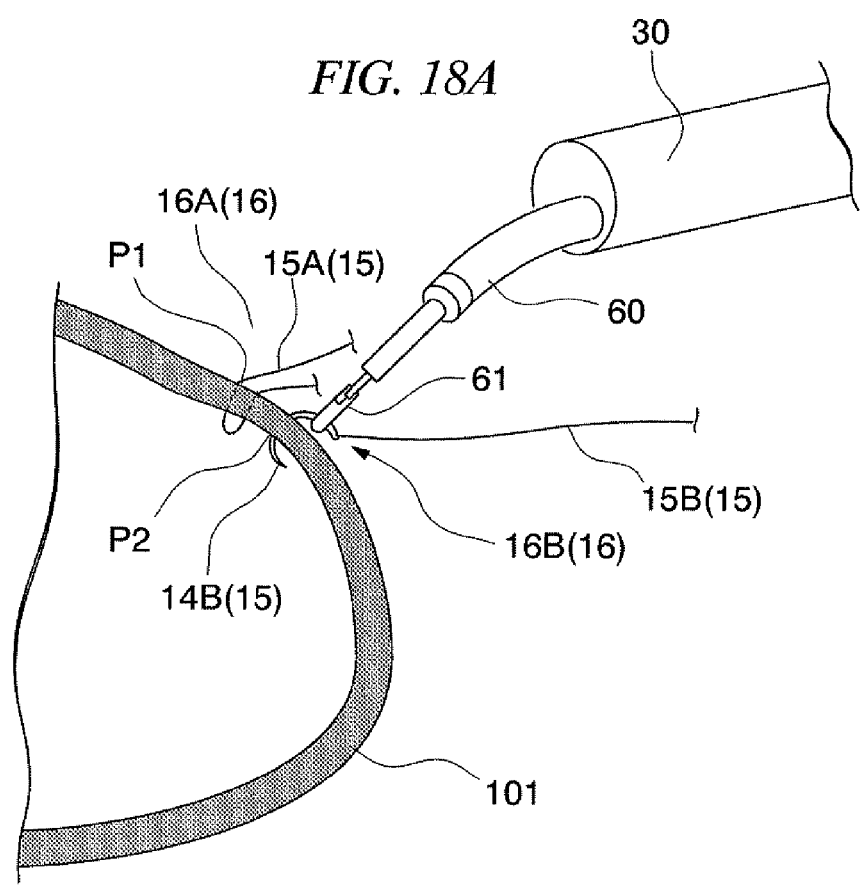
FIG. 18A is a view for explaining the action in a modification of the same biological tissue transfer method and same treatment method.
Figure 18B:
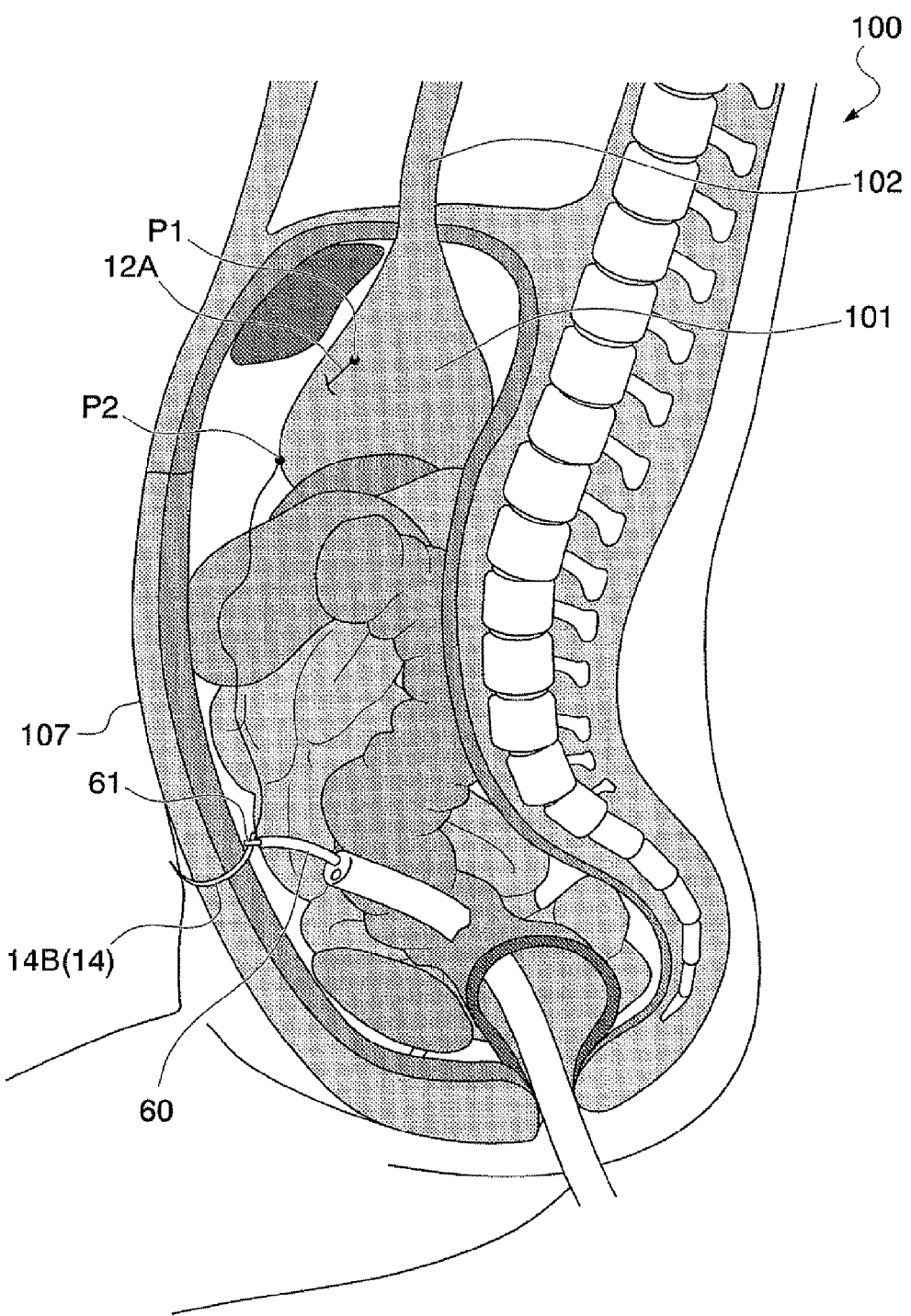
FIG. 18B is a view for explaining the action for pulling the first traction member to the outside of the body in this same modification.

Next, the biological tissue transfer method and the biological tissue treatment method according to a modification of the present invention will now be explained with reference to FIGS. 18A and 18B. FIG. 18A is a view for explaining the biological tissue transfer method and the biological tissue treatment method according to the present modification. FIG. 18B is a view for explaining the action of withdrawing the first traction member 10A to the outside of the body in this modification.

In this modification, the first traction member attaching step S1, the second traction member attaching step S2 and the withdrawing step S3 differ from the preceding embodiments. In addition, in this modification, a traction member 16 (first traction member 16A and second traction member 16B) is employed in place of the traction member 10 and the indwelling implement 20 used in the preceding embodiment, this traction member 16 having a traction suture 15 which has a curved needle 14 attached to one end thereof.

As shown in FIG. 18A, in the first traction member attaching step S1 and the second traction member attaching step S2 in this modification, the traction suture 15 is guided to the first position P1 and the second position P2 after passing through the inside of an endoscope which has been inserted into the body cavity, without employing the aforementioned indwelling implement 20 (the endoscope 30 explained in the preceding embodiment may be used as shown in FIG. 18A for example). Next, an endoscopic grasping forceps 60 having a grasping part 61 for grasping a curved or a straight needle 14 is inserted into the endoscope, and the curved or straight needle 14 which is attached to one end of the traction suture 15 is passed through the stomach wall to fix the traction suture 15 to the stomach wall. Note that it is also acceptable to firmly affix the traction suture 15 to the stomach wall by passing the curved or straight needle 14 through the stomach wall multiple times. This concludes the first traction member attaching step S1 and the second traction member attaching step S2, and the procedure progresses to the withdrawing step S3.

As shown in FIG. 18B, in the withdrawing step S3, the curved or straight needle 14 is moved to the withdrawal positions P3,P4 while being grasped by the grasping part 61 of the endoscopic grasping forceps 60 which were inserted into the endoscope 30. The curved or straight needle 14 is then pushed from the inside to the outside of the body at the withdrawal positions P3,P4, and the traction suture 15 is withdrawn to the outside of the body.

Note that once treatment step S5 is concluded in the case where strongly affixing the traction suture 15 to the stomach wall by passing the needle multiple times through the stomach wall, the endoscope 30 is employed to cut the traction suture 15 and the traction suture 15 is pulled to the outside of the body. In the case where using a traction suture 15 formed of a bioabsorbable material, it is not problematic to leave behind remnants, such as the suture portions within the stomach wall, of the traction suture 15.

This method has the same effects as those of the method explained in the preceding embodiment.

Further, in this modification, it is not necessary to carry out piercing using the piercing needle 21 of an indwelling implement 20 explained in the preceding embodiment. Thus, the stress on the patient 100 can be reduced.

Figure 19:
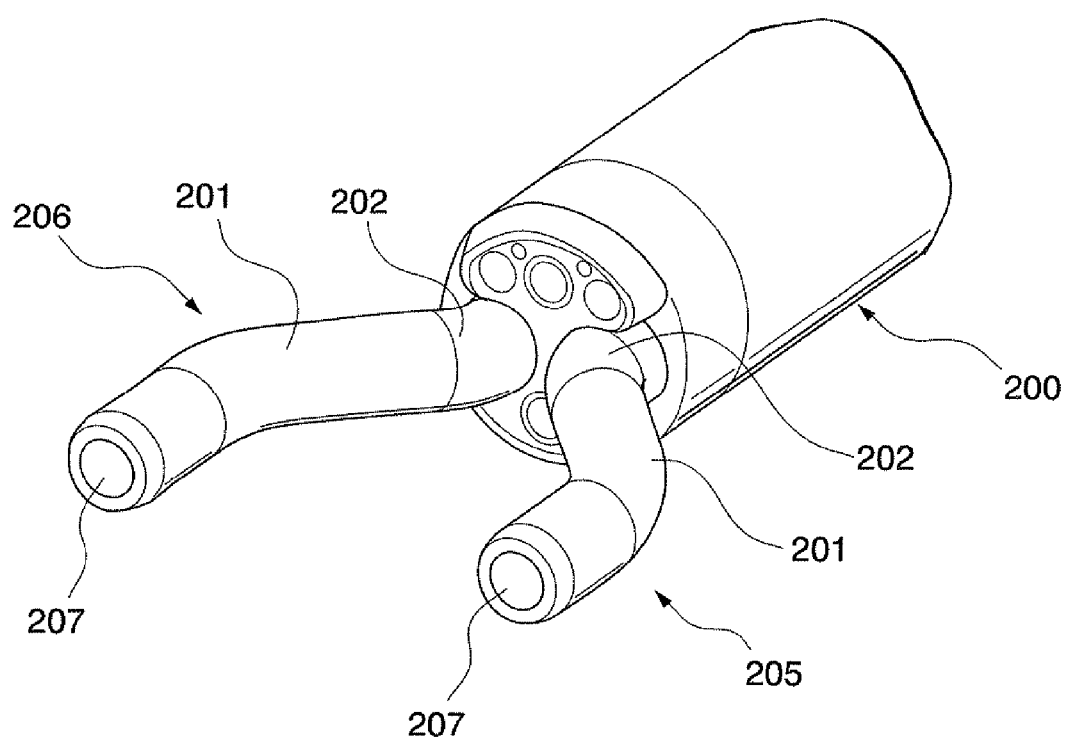
FIG. 19 is a view showing an example of a treatment endoscope which can be used in the same treatment method.

Further, in the preceding embodiment and modification, an example of using the endoscope 30 is explained. However, the present invention is not limited thereto. A treatment endoscope 200 shown in FIG. 19 may be used instead of a viewing endoscope, such as the endoscope 30. The treatment endoscope 200 is provided with two arms 205, 206 at a distal end thereof. Both of the arms 205, 206 have bending portions 201, 202 and a channel for a treatment tool to freely pass through. An aperture 207 communicating with the channel is formed on a distal end of each arm 205, 206. Thereby, the present application can be performed with various treatment tools which protrude from the apertures 207 of the treatment endoscope 200.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

Accordingly, the invention is not to be considered as being limited by the foregoing description, and is only limited by the scope of the appended claims.

What is claimed:

1. A biological tissue transfer method for transferring within a body a stomach on which a treatment target site is present, the method comprising:
   (a) attaching part of a first traction member to a first position which is on the stomach and is different from the target site, and which is different from a connecting position at which an esophagus is connected to a thoracic diaphragm which supports the esophagus within the body;
   (b) attaching part of a second traction member to a second position which is on the stomach and is different from the target site, the connecting position, and the first position, and which serves as an apex of a triangle formed together with the connecting position and the first position, the triangle surrounding the target site, the triangle formed in part by a first straight line extending through the connecting position and the first position and a second straight line extending through the connecting position and the second position;
   (c) extending the first traction member along the first straight line in a first direction extending from the connecting position to the first position, and extending the second traction member along the second straight line in a second direction extending from the connecting position to the second position;
   (d) transferring the stomach within the body by applying traction on the first traction member along the first straight line in the first direction and by applying traction on the second traction member along the second straight line in the second direction; and
   (e) performing a surgical procedure on the target site after transferring the stomach.

2. The biological tissue transfer method according to claim 1, wherein
   in the step (c), the first traction member is withdrawn toward an outside of the body and the second traction member is withdrawn to the outside of the body, and
   in the step (d), a portion of the first traction member withdrawn to the outside of the body and a portion of the second traction member withdrawn to the outside of the body are grasped, and traction is applied to at least one of the first traction member and the second traction member.

3. The biological tissue transfer method according to claim 2, wherein
   in the step (d), traction toward the outside of the body is applied to one of either the first traction member or the second traction member by differing an amount of traction applied at the first position on the stomach from the first traction member and an amount of traction applied at the second position on the stomach from the second traction member.

4. The biological tissue transfer method according to claim 1, wherein
   a first rod, which is wider than a diameter of the first traction member, is connected to the first traction member, and
   in the step (a), the first rod is inserted into a cylindrical piercing needle, the piercing needle is pushed into the stomach at the first position from an outside of the body, the first rod and a portion of the first traction member which is connected to the first rod are released inside the stomach, while another part of the first traction member is released inside the body and external to the stomach, and the piercing needle following release of the first rod and the first traction member is pulled out of the body.

5. The biological tissue transfer method according to claim 4, wherein
   the first rod has a through hole through which the first traction member is inserted,
   the first traction member is connected to the first rod by insertion into the through hole at a center and in a longitudinal direction of the first rod, in the step (c), ends of the first traction member are withdrawn to the outside of the body, and the first traction member is pulled out of the body by applying traction to one of the ends of the first traction member after the step (d), leaving the first rod inside the stomach.

6. The biological tissue transfer method according to claim 1, wherein a second rod, which is wider than a diameter of the second traction member, is connected to the second traction member, and in the step (b), the second rod is inserted into a cylindrical piercing needle, the piercing needle is pushed into the stomach at the second position from an outside of the body, the second rod and a portion of the second traction member which is connected to the second rod are released inside the stomach, while another part of the second traction member is released inside the body and external to the stomach, and the piercing needle following release of the second rod and the second traction member is pulled out of the body.

7. The biological tissue transfer method according to claim 6, wherein the second rod has a through hole through which the second traction member is inserted, the second traction member is connected to the second rod by insertion into the through hole at a center and in a longitudinal direction of the second rod, in the step (c), ends of the second traction member are withdrawn to the outside of the body, and the second traction member is pulled out of the body by applying traction to one of the ends of the second traction member after the step (d), leaving the second rod inside the stomach.

8. The biological tissue transfer method according to claim 1, wherein in the steps (a) and (b), a first needle, which is capable of being pushed into the stomach, is connected to the first traction member, a second needle, which is capable of being pushed into the stomach, is connected to the second traction member, an endoscope is inserted from an outside to an inside of the body, the first traction member and the second traction member are guided to the inside of the body using the endoscope, the first needle is grasped by the endoscope and the first traction member is fixed to the stomach using the first needle, and the second needle is grasped by the endoscope and the second traction member is fixed to the stomach using the second needle, and in the step (c), the first needle and the second needle pass through a body wall to the outside of the body using the endoscope, and the first traction member attached to the first needle and the second traction member attached to the second needle are pulled toward the outside of the body.

9. The biological tissue transfer method according to claim 1, wherein, in the step (c), first and second penetrating holes are formed in an abdominal wall and the first traction member and the second traction member are pulled out of the body via the first penetrating hole and second penetrating hole, respectively.

10. A biological tissue treatment method employing the biological tissue transfer method according to claim 1, wherein a treatment is performed using an endoscope in a surrounding space within which the stomach has been transferred following completion of the step (d).

11. A biological tissue treatment method employing the biological tissue transfer method according to claim 1, wherein a treatment is performed using Fundoplication surgery following completion of the step (d).

* * * * *